US00PP13522P3

(12) United States Plant Patent
Lemon

(10) Patent No.: US PP13,522 P3
(45) Date of Patent: Jan. 28, 2003

(54) VARIETY OF GERANIUM PLANT NAMED 'BRAVO'

(75) Inventor: David Lemon, County of Santa Barbara, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/877,299

(22) Filed: Jun. 8, 2001

(65) Prior Publication Data

US 2002/0188991 P1 Dec. 12, 2002

(51) Int. Cl.[7] ..... A01H 5/00

(52) U.S. Cl. ..... Plt./331

(58) Field of Search ..... Plt./331

*Primary Examiner*—Bruce R. Campell
*Assistant Examiner*—Annette Para
(74) *Attorney, Agent, or Firm*—Webb Ziesenheim Logsdon Orkin & Hanson, P.C.

(57) ABSTRACT

A new and distinct early flowering regal geranium plant with red-purple and white bicolored petals having above medium green foliage.

1 Drawing Sheet

CLASSIFICATION

*Pelargonium×domesticum* (regal geranium).

VARIETAL DENOMINATION

'Bravo'.

BACKGROUND OF THE INVENTION

The present invention comprises a new and distinct cultivar of *Pelargonium×domesticum* known by the varietal name 'Bravo'. The new variety was discovered in a selected breeding program in Lompoc, Calif. The new variety is a selection from the cross of unpatented proprietary breed variety Seedling Purple Bicolor '607', the female parent and 'Lois', the male parent, (U.S. Plant Pat. No. 10,000). The bicolor flower pattern differs from those of 'Lois' and 'Jewel' (U.S. Ser. No. 09/877,168). The new variety was first asexually reproduced by cuttings in Connellsville, Pa. The new variety has been trial and field tested at Connellsville and has been found to retain its distinctive characteristics and remain true to type through successive propagations.

The cultivar, when grown in a glass greenhouse in Connellsville, Pa. using natural light and temperatures of 60° F. night and 68° F. day, has a response time of 13 weeks from a rooted cutting to flowering in a 6 inch pot. The response time was determined on plants grown in soilless media employing constant fertilizer 150–200 parts per million of nitrogen and potassium in full light.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar at 10 weeks grown from a rooting cutting. The data which defines these characteristics were collected by asexual reproductions carried out by Oglevee, Ltd. in Connellsville, Pa. The color readings were taken on a plant under 200–220 foot candles of fluorescent cool white light. Color references are primarily to The R.H.S. Colour Chart of The Royal Horticultural Society of London.

PLANT

Form: Medium mound trailing and cascading.
Height: 21–24 cm from soil to top of foliage.
Growth: Upright, free basal branching.
Strength: Dose not require artificial support.
Foliage: Stalked leaf attachment, medium green foliage.
Rooting time: Roots visible to outside of artificial dirt plug in 14–21 days.
Leaves:
- *Size.*—Length: 6–8.5 cm. Width: 9.5–11 cm.
- *Shape.*—Reniform; truncate base.
- *Margin.*—Serrated; lobed.
- *Texture.*—Leathery; pubescent.
- *Color.*—Upper surface: Green Group 137A. Lower surface: Green Group 137C.
- *Ribs and veins.*—Venation: Palmate. Color: Yellow-Green Group 146D.

Petioles:
- *Color.*—Yellow-Green Group 146D.
- *Length.*—4–8.2 cm.

Stem:
- *Color.*—Yellow-Green Group 144B.
- *Internode length.*—1.5–3 cm.

THE BUD

Shape just prior to anthesis:
- *Overall.*—Elliptical to round cluster.
- *Individual bud.*—Elliptical.

Size when just showing color:
- *Overall.*—3–6 cm across.
- *Individual bud.*—2–2.8 cm long; 0.9–1.1 cm wide.

Number of buds per cluster: 3–7.

INFLORESCENCE

Blooming habit: Continuous; large florets forming full flower heads.

*Size.*—10–12 cm.

*Borne.*—Flowers on umbel; umbel on pedicel; pedicel on peduncle.

Flowers:

*Form.*—Opened to slightly cupped, petals overlap; moderately ruffled.

*Number of flowers per umbel.*—3–7.

*Size.*—Diameter: 8.5–9.5 cm. Depth: 3.5–4.5 cm.

*Petals.*—Color: Upper surface: Lower Petals: White Group 155C with a brush of Red-Purple Group 60B in the center of the petal. Upper Petals: Base and outer edge are White Group 155C. The center of the petal is Greyed-Purple Group 187C fading in Greyed-Purple Group 187D and Red-Purple Group 61A and Red-Purple Group 61B. The veins in bottom white part start at the center with Red-Purple Group 61A fading towards the edge to Red-Purple Group 61B. The veins in the center blotch are Greyed-Purple Group 187A fading towards the edge. Lower surface: Lower Petals: White Group 155C with a brush of Red-Purple Group 60D. Upper Petals: The base and outer edge of White Group 155C is bigger than on the upper surface, the blotch in the center of Greyed-Purple Group 187C is smaller than on the upper surface. It fades towards the edge in the Greyed-Purple Group 187D and Red-Purple Group 61A and Red-Purple Group 61B. There are three to four main veins on the lower side of the upper petals with Greyed-Purple Group 186C, the rest of the veins are identical with the upper side. Shape: Obovate. Size: Length: 5–5.5 cm. Width: 3.3–4.7 cm. Margin: Entire. Number per floret: 5.

Texture and appearance: Smooth, satiny.

Tonality from a distance: Shining purple upper petals in contrast to the almost completely white lower petals above medium green foliage.

Petaloids: None observed.

Pedicel:

*Length.*—2.2–2.7 cm.

*Color.*—Yellow-Green Group 146A.

Peduncle:

*Length.*—4.5–5.4 cm.

*Color.*—Yellow-Green Group 146A.

Disease/pest resistance: No unusual susceptibility to diseases or pests has been noted to date.

Lasting quality: Individual umbels will last in the home environment for 4–6 weeks. Overall flowering will continue as long as conditions remain cool at night with plenty of light provided.

Fragrance: None.

REPRODUCTIVE ORGANS

Stamens:

*Quantity.*—7.

*Anthers.*—3–4 mm.

*Filaments.*—Length: 1.4–1.8 cm. Color: White fading into pink-purple at the top. Pollen: Golden orange.

Pistils:

*Number.*—One.

*Length.*—2.2–2.5 cm.

*Stigma.*—Number: One; five or six parted. Color: Greyed-Purple Group 187A.

*Style.*—Length: 1.6–1.8 cm. Color: Greyed-Purple Group 187D.

Ovaries:

*Completeness.*—Superior.

*Pubescence.*—Greatly pubescent.

*Length.*—6–8 mm.

*Width.*—3 mm.

*Color.*—Yellow-Green Group 144A.

Fruit: None observed.

GENERAL CHARACTERISTICS

1. 'Bravo' is a very early flowering plant.
2. Bravo is a more compact plant than parents.
3. Good bicolor.
4. Plant type is good.

I claim:

1. A new and distinct variety of geranium plant substantially as shown and described.

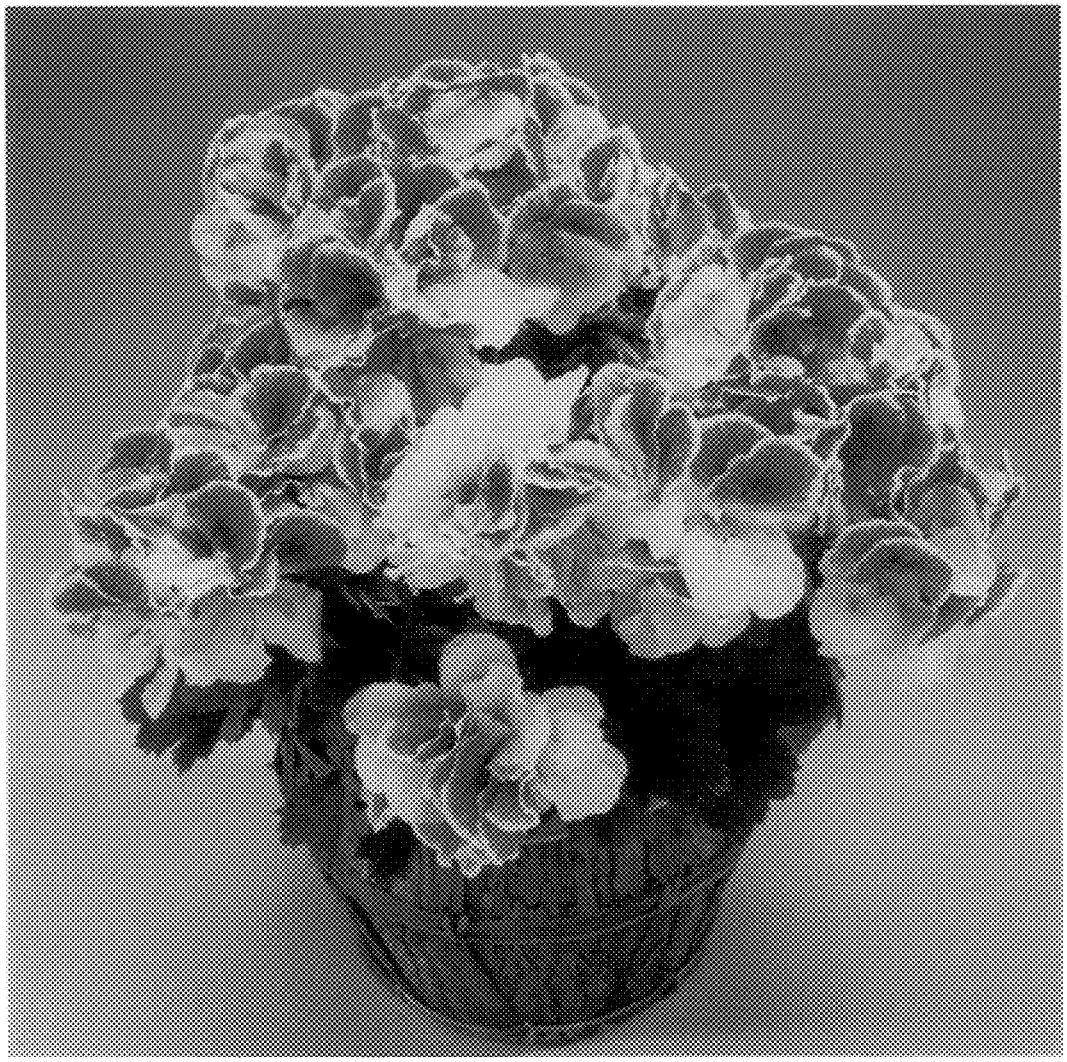

* * * * *